(12) United States Patent
Mason et al.

(10) Patent No.: US 9,757,043 B2
(45) Date of Patent: Sep. 12, 2017

(54) METHOD AND SYSTEM FOR DETECTION OF RESPIRATORY VARIATION IN PLETHYSMOGRAPHIC OXIMETRY

(71) Applicant: Los Angeles Biomedical Research Institute at Harbor-UCLA Medical Center, Torrance, CA (US)

(72) Inventors: Gregory R. Mason, Manhattan Beach, CA (US); John M. Criley, Palos Verdes, CA (US); Stuart R. Criley, Palos Verdes Estates, CA (US)

(73) Assignee: LOS ANGELES BIOMEDICAL RESEARCH INSTITUTE AT HARBOR-UCLA MEDICAL CENTER, Torrance, CA (US)

( * ) Notice: Subject to any disclaimer, the term of this patent is extended or adjusted under 35 U.S.C. 154(b) by 146 days.

(21) Appl. No.: 13/919,878

(22) Filed: Jun. 17, 2013

(65) Prior Publication Data

US 2013/0281805 A1 Oct. 24, 2013

Related U.S. Application Data

(60) Continuation-in-part of application No. 13/404,265, filed on Feb. 24, 2012, now Pat. No. 8,465,434, which is a division of application No. 12/315,813, filed on Dec. 5, 2008, now Pat. No. 8,128,569.

(60) Provisional application No. 60/992,973, filed on Dec. 6, 2007.

(51) Int. Cl.
| | |
|---|---|
| *A61B 5/08* | (2006.01) |
| *A61B 5/0205* | (2006.01) |
| *A61B 5/024* | (2006.01) |
| *A61B 5/0452* | (2006.01) |

(52) U.S. Cl.
CPC ........ *A61B 5/0205* (2013.01); *A61B 5/02416* (2013.01); *A61B 5/0452* (2013.01); *A61B 5/0816* (2013.01)

(58) Field of Classification Search
CPC .......................... A61B 5/0205; A61B 5/02416
See application file for complete search history.

(56) References Cited

U.S. PATENT DOCUMENTS

| | | | |
|---|---|---|---|
| 5,144,956 | A | 9/1992 | Souma |
| 5,632,272 | A | 5/1997 | Diab et al. |
| 6,002,952 | A | 12/1999 | Diab et al. |
| 6,129,675 | A | 10/2000 | Jay |
| 6,157,850 | A | 12/2000 | Diab et al. |
| 6,263,222 | B1 | 7/2001 | Diab et al. |

(Continued)

OTHER PUBLICATIONS

American Thoracic Society, "Standards for the Diagnosis and Care of Patients with Chronic Obstructive Pulmonary Disease", *Am J Respir Crit Care Med*, 152, (1995), S77-S121.

(Continued)

*Primary Examiner* — Christian Jang
(74) *Attorney, Agent, or Firm* — Foley & Lardner LLP

(57) ABSTRACT

A method and system for detection of pulsus paradoxus are provided. In one embodiment, the method includes determining a power spectrum density for a plethysmographic waveform and identifying pulsus paradoxus based on the power spectrum density. The power spectrum density may include a first wave peak indicative of a respiratory rate and a second wave peak indicative of a heart rate. Pulsus paradoxus can be identified by comparing a height of the first wave peak and a height of the second wave peak.

14 Claims, 9 Drawing Sheets

(56) References Cited

U.S. PATENT DOCUMENTS

| | | | |
|---|---|---|---|
| 6,325,761 | B1 | 12/2001 | Jay |
| 6,334,065 | B1 | 12/2001 | Al-Ali et al. |
| 6,387,053 | B1 | 5/2002 | Pessenhofer |
| 6,650,917 | B2 | 11/2003 | Diab et al. |
| 6,699,194 | B1 | 3/2004 | Diab et al. |
| 6,745,060 | B2 | 6/2004 | Diab et al. |
| 6,770,028 | B1 | 8/2004 | Ali et al. |
| 6,869,402 | B2 | 3/2005 | Arnold |
| 7,044,917 | B2 | 5/2006 | Arnold |
| 7,215,984 | B2 | 5/2007 | Diab et al. |
| 7,292,883 | B2 | 11/2007 | De Felice et al. |
| 2001/0012917 | A1 | 8/2001 | Inukai et al. |
| 2003/0120164 | A1 | 6/2003 | Nielsen et al. |
| 2004/0044276 | A1 | 3/2004 | Arnold |
| 2005/0107712 | A1 | 5/2005 | Arnold |
| 2005/0228302 | A1 | 10/2005 | Dalgaard et al. |
| 2005/0251056 | A1 | 11/2005 | Gribkov |
| 2006/0253040 | A1 | 11/2006 | Stergiopoulos et al. |
| 2007/0125378 | A1 | 6/2007 | Heinonen |
| 2008/0064965 | A1 | 3/2008 | Jay et al. |
| 2008/0269625 | A1 | 10/2008 | Halperin et al. |

OTHER PUBLICATIONS

Arnold, D. H., et al., "Estimation of airway obstruction using oximeter plethysmograph waveform data", *Respir. Res.*, 6(1),(2005), 65.

Bacon, A. K., "Crisis management during anaesthesia: pnuemothorax", *Quality and Safety in Health Care*, 14(18), (2005), 5 pages.

Barach, P., "Pulsus Paradoxus", *Hospital Physician*, 1, (Jan. 2000), 49-50.

Barbieri, R., et al., "Model Dependency of Multivariate Autoregressive Spectral Analysis", *IEEE Engineering in Medicine and Biology*, 16(5), (Sep.-Oct. 1997), 74-85.

Baselli, G., et al., "Spectral Decomposition in Multichannel Recordings Based on Multivariate Parametric Identification", *IEEE Transactions on Biomedical Engineering*, 44(11), (Nov. 1997), 1092-1101.

Bilchick, K. C., et al., "Paradoxical physical findings described by Kussmaul: pulsus paradoxus and Kussmaul's sign", *The Lancet*, vol. 359, No. 9321, (Jun. 1, 2002), 1940-1942.

Biosig Project, "BioSig for Octave and Matlab", accessed via Internet: http://biosig.sourceforge.net on Nov. 13, 2005, 1 page.

Brathwaite, Collin E., et al., "Continuous Pulse Oximetry and the Diagnosis of Pulmonary Embolism in Critically Ill Trauma Patients", *The Journal of Trauma*, vol. 33, No. 4, (Oct. 1992), 528-531.

Computational Intelligence Group, "The R Project for Statistical Computing", accessed via Internet: http://www.r-project.org on Nov. 13, 2005, 1 page.

Curtiss, Edward I., et al., "Pulsus paradoxus: Definition and relation to the severity of cardiac tamponade", *Am Heart J*, 115(2), (1988), 391-398.

Deshmane, A. V., *False Arrhythmia Alarm Suppression Using ECG, ABP, and Photoplethysmogram*, Massachusetts Institute of Technology, (Sep. 2009), 93 pp.

Duhamel, P., "Implementation of "Split-Radix" FFT Algorithms for Complex, Real, and Real-Symmetric Data", *IEEE Transactions on Acoustics, Speech and Signal Processing*, 34(2), (Apr. 1986), 285-295.

Fowler, N. O., "Cardiac tamponade: A Clinical or an Echocardiographic Diagnosis?", *Circulation*, 87(5), (May 1993), 1738-1741.

Fowler, N. O., "Physiology of Cardiac Tamponade and Pulsus Paradoxus, II: physiological, circulatory, and pharmacological responses in cardiac tamponade", *Mod Concepts Cardiovasc Disease*, vol. 47, No. 12, (Dec. 1978), 115-118.

Frey, B., et al., "Pulse oximetry for assessment of pulsus paradoxus: a clinical study in children", *Intensive Care Medicine*, 24, (1998), 242-246.

Guberman, B. A., et al., "Cardiac Tamponade in Medical Patients", *Circulation*, 64(3), (Sep. 1981), 633-640.

Hartert, T. V., et al., "Use of Pulse Oximetry to Recognize Severity of Airflow Obstruction in Obstructive Airway Disease", *Chest*, 115(2), (Feb. 1999), 475-481.

Hegde, A., et al., "Investigating Spatio-Temporal Synchronizations in Epileptic ECOG", *University of Computational NeuroEngineering Laboratory*, www.dnel.ufl.edu/files/1098114461.ppt,.

Heideman, M. T., et al., "Gauss and the History of the Fast Fourier Transform", *IEEE Acoustics, Speech and Signal Processing Magazine*, 1, (Oct. 1984), 14-21.

Irizarry, R. A., "Local Regression with Meaningful Parameters", *American Statistician*, 55, (2001), 72-79.

Jardin, F., et al., "Mechanism of paradoxic pulse in bronchial asthma", *Circulation*, 66(4), (1982), 887-894.

Kolba, D. P., "A Prime Factor FFT Algorithm Using High-Speed Convolution", *IEEE Transactions on Acoustics, Speech and Signal Processing*, 25(4), (Aug. 1977), 281-294.

Kussmaul, A., "Ueber schwielige Mediastino-Pericarditis und den paradoxen Puls", *Berliner Klinische Wochenschrift*, 10, (1873), 433-435, 445-449 and 461-464.

La Biomed, International Search Report and Written Opinion dated Jan. 7, 2010 for PCT/US2009/061930.

La Biomed, International Preliminary Report on Patentability mailed May 5, 2011 for PCT/US2009/061930.

La Biomed, Non-final Office Action mailed Jun. 6, 2011 for U.S. Appl. No. 12/315,813, 13 pages.

La Biomed, Final Office Action mailed Oct. 11, 2011 for U.S. Appl. No. 12/315,813, 8 pages.

Laishley, R. S., et al., "Tension Pneumothorax and Pulse Oximetry", *British Journal of Anaesthesia*, 66, (1991), 250-252.

Levine, Marc J., et al., "Implications of Echocardiographically Assisted Diagnosis of Pericardial Tamponade in Contemporary Medical Patients: Detection Before Hemodynamic Embarrassment", *J Am Coll Cardiol.*, vol. 17, No. 1, (Jan. 1991).

McCaig, L. F., "National Hospital Ambulatory Medical Care Survey: 2003 Emergency Department Survey", *Advance Data*, 358, (May 26, 2005), 38 pages.

Mower, W. R., "Pulse Oximetry as a Fifth Pediatric Vital Sign", *Pediatrics*, 99, (1997), 681-686.

National Center for Health, Statistics, "Fast Stats from A to Z: Asthma", accessed via Internet: http://www.cdc.gov/nchs/fastats/asthma.htm on Jul. 12, 2005, 2 pages.

National Heart, Blood & Lung, Institute, "Guidelines for the Diagnosis and Management of Asthma", *Journal of Allergy and Clinical Immunology*, vol. 88, No. 3, Part 2, (Sep. 1991), 496-502.

National Heart, Blood & Lung, Institute, "Practical Guide for the Diagnosis and Management of Asthma", *NIH Publication No. 97-4053*, 60 pages.

Netlib.com, "Netlib libraries for computational mathematics", Accessed via Internet: http://www.netlib.org/liblist.html on Nov. 13, 2005, 2 pages.

Plummer, M., et al., "Integrated ARMA Time Series Modelling", *Lund University Center for Mathematical Sciences*, http://www.maths.lth.se/help/R/.R/library/fSeries/html/A1-armaModelling.html, retrieved Jun. 18, 2010, 8 pages.

Rao, Y. N., "A Fast On-line Generalized Eigendecomposition Algorithm for Time Series Segmentation", *IEEE Symposium on Adaptive Systems for Signal Proc. Commun. and Controls*, Alberta, Canada, (2000), 266-271.

Rayner, J., et al., "Continuous Noninvasive Measurement of Pulsus Paradoxus Complements Medical Decision Making in Assessment of Acute Asthma Severity", *Chest*, 130(3), (Sep. 2006), 754-765.

Reddy, P. S., et al., "Cardiac Tamponade", *Cardiology Clinics*, vol. 8, No. 4, (Nov. 1990), 627-637.

Reddy, P. S., et al., "Cardiac Tamponade: Hemodynamic Observations in Man", *Circulation*, 58(2), (Aug. 1978), 265-272.

Reddy, P. S., et al., "Spectrum of Hemodynamic Changes in Cardiac Tamponade", *Am J Cardiol*, 66, (Dec. 15, 1990), 1487-1491.

(56) References Cited

OTHER PUBLICATIONS

Roy, C. L., et al., "Does This Patient With a Pericardial Effusion Have Cardiac Tamponade?", *JAMA*, 297(16), (Apr. 25, 2007), 1810-1818.

Salyer, J. W., "Neonatal and Pediatric Pulse Oximetry", *Respiratory Care*, 48(4), (2003), 386-396.

Shamir, M., et al., "Pulse oximetry plethysmographic waveform during changes in blood volume", *British Journal of Anaesthesia*, 82(2), (1999), 178-181.

Singh, S., et al., "Right ventricular and right atrial collapse in patients with cardiac tamponade—a combined echocardiographic and hemodynamic study", *Circulation*, 70(6), (Dec. 1984), 966-971.

Systat Software Corporation, "AutoSignal 1.7", Accessed via Internet: http://www.systat.com/products/AutoSignal on Nov. 12, 2005, 3 pages.

Tamburro, R. F., "Detection of Pulsus Paradoxus Associated with Large Pericardial Effusions in Pediatric Patients by Analysis of the Pulse-Oximetry Waveform", *Pediatrics*, 109(4), (Apr. 2002), 673-677.

Thong, T., et al., "Nonlinear Reconstruction of Over-Sampled Coarsely Quantized Signals", *IEEE 45th Midwest Symposium on Circuits and Systems*, Tulsa, Oklahoma, vol. 2, (Aug. 4-7, 2002), 416-417.

Tremper, K. K., "Pulse Oximetry's Final Frontier", *Critical Care Medicine*, 28(5), (May 2000), 1684-1685.

Van Steenis, H. G., "Time-Frequency Parameters of Heart-Rate Variability", *IEEE Engineeringin Medicine and Biology*, 21(4),(Jul.-Aug. 2002), 46-58.

Varri, A., et al., "Standards for Biomedical Signal Databases", *IEEE Engineering in.Medicine and Biology*, 20(3), (May-Jun. 2001), 33-38.

Welch, P.D., "The Use of Fast Fourier Transform for the Estimation of Power Spectra: A Method Based on Time Averaging Over Short, Modified Periodograms," *IEEE Transactions on Audio Electroacoustics*, vol. 15:2 (Jun. 1967), 70-73.

Winkler, R., et al., *Statistics: Probability, Inference, and Decision*, 2nd Edition, Holt Reinhart Winston, (1975), 643-655.

Working Group on Blood Pressure, and Heart Rate Variability of T., "Glossary of Terms Used in Time Series Analysis of Cardiovascular Data", Accessed via Internet: http://www.cbi.dongnocchi.it/glossary/Glossary.html on Nov. 13, 2005, 7 pages.

US Office Action dated Apr. 7 2016, from related U.S. Appl. No. 12/604,346.

Brenner, Judith. "Bedside Rounds#1: Why is a pulsus paradoxus not a paradox?". Feb. 1, 2007.

Final office action received in U.S. Appl. No. 12/604,346 on Jul. 30, 2014, 12 pages.

Final office action received in U.S. Appl. No. 12/604,346 on May 8, 2013, 8 pages.

Jithesh, K. "Review Article: Pulsus Paradoxus (Reversed Bernheim sign)". Apr. 26, 2006. p. 1-4.

Non-Final office action received in U.S. Appl. No. 12/604,346 on Dec. 27, 2013, 11 pages.

Non-Final office action received in U.S. Appl. No. 12/604,346 on Jun. 21, 2015, 7 pages.

Non-Final office action received in U.S. Appl. No. 12/604,346 on Sep. 19, 2012, 7 pages.

Non-Final office action received in U.S. Appl. No. 12/604,346 on Jan. 13, 2015, 13 pages.

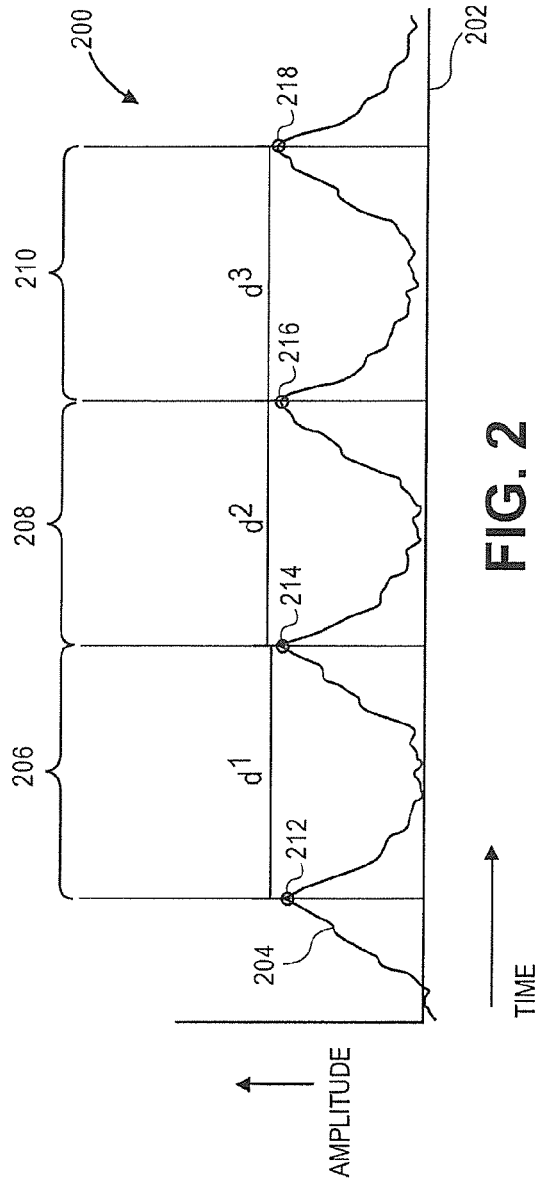
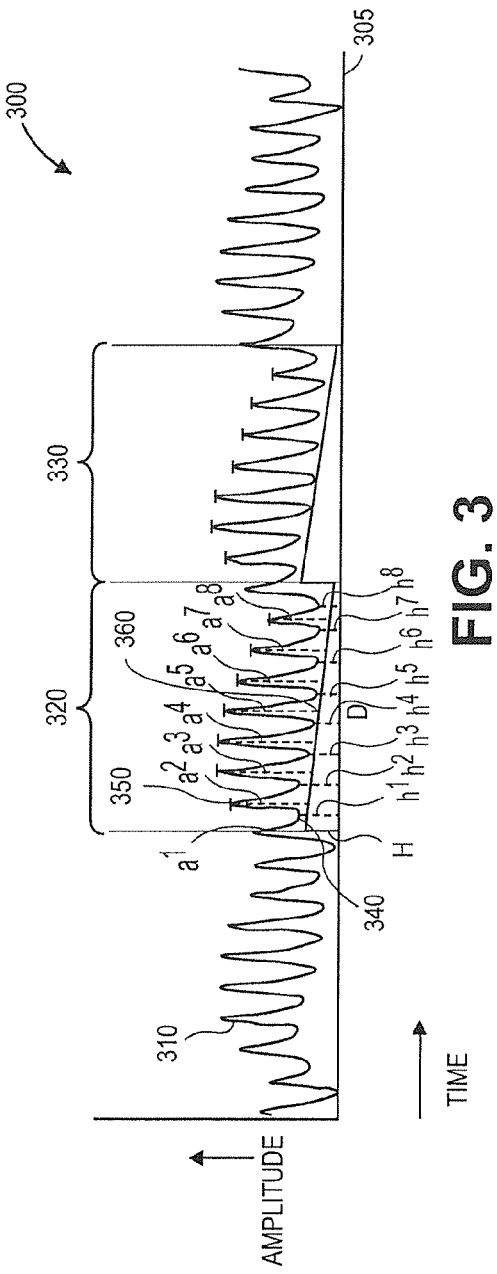

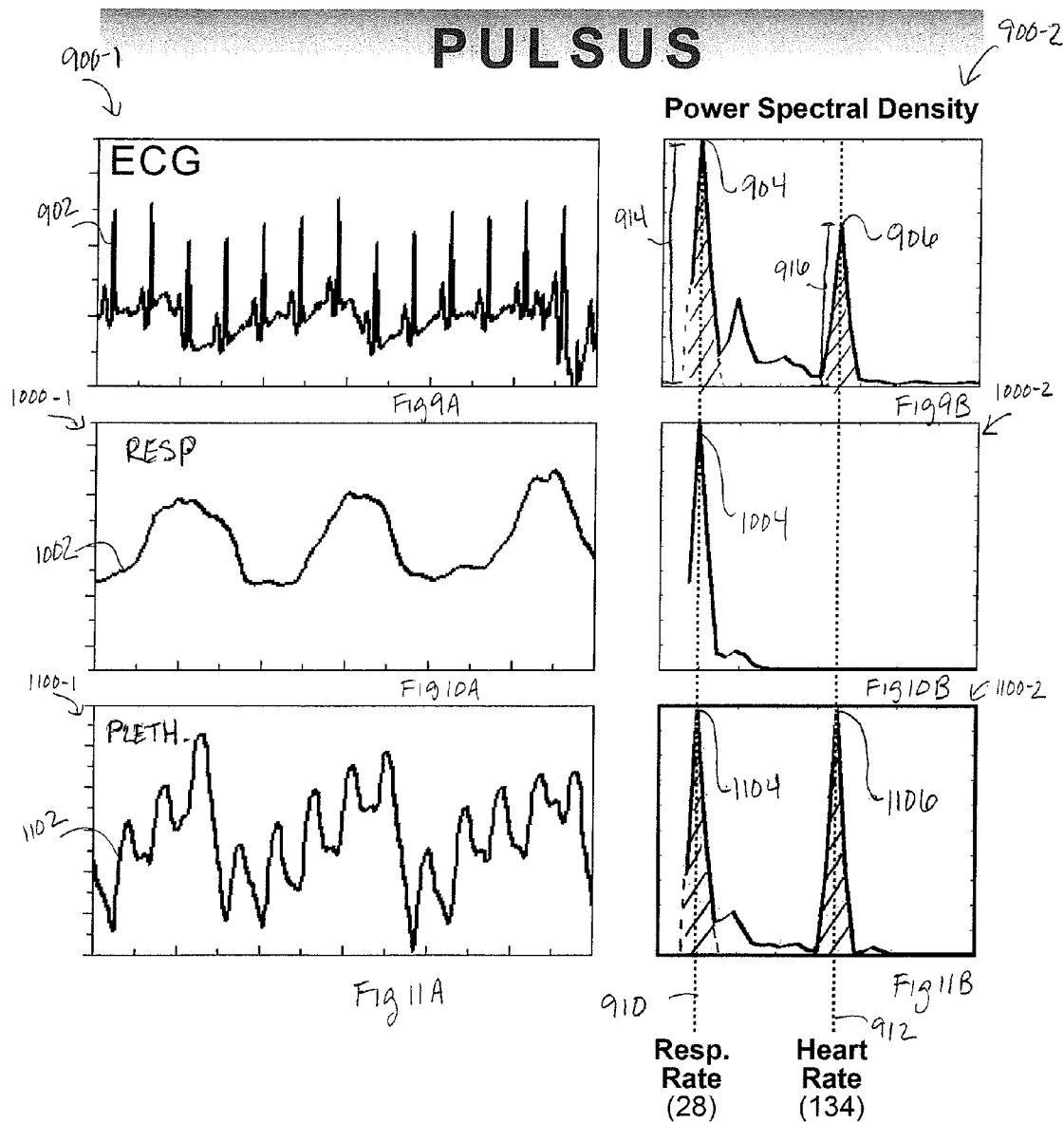

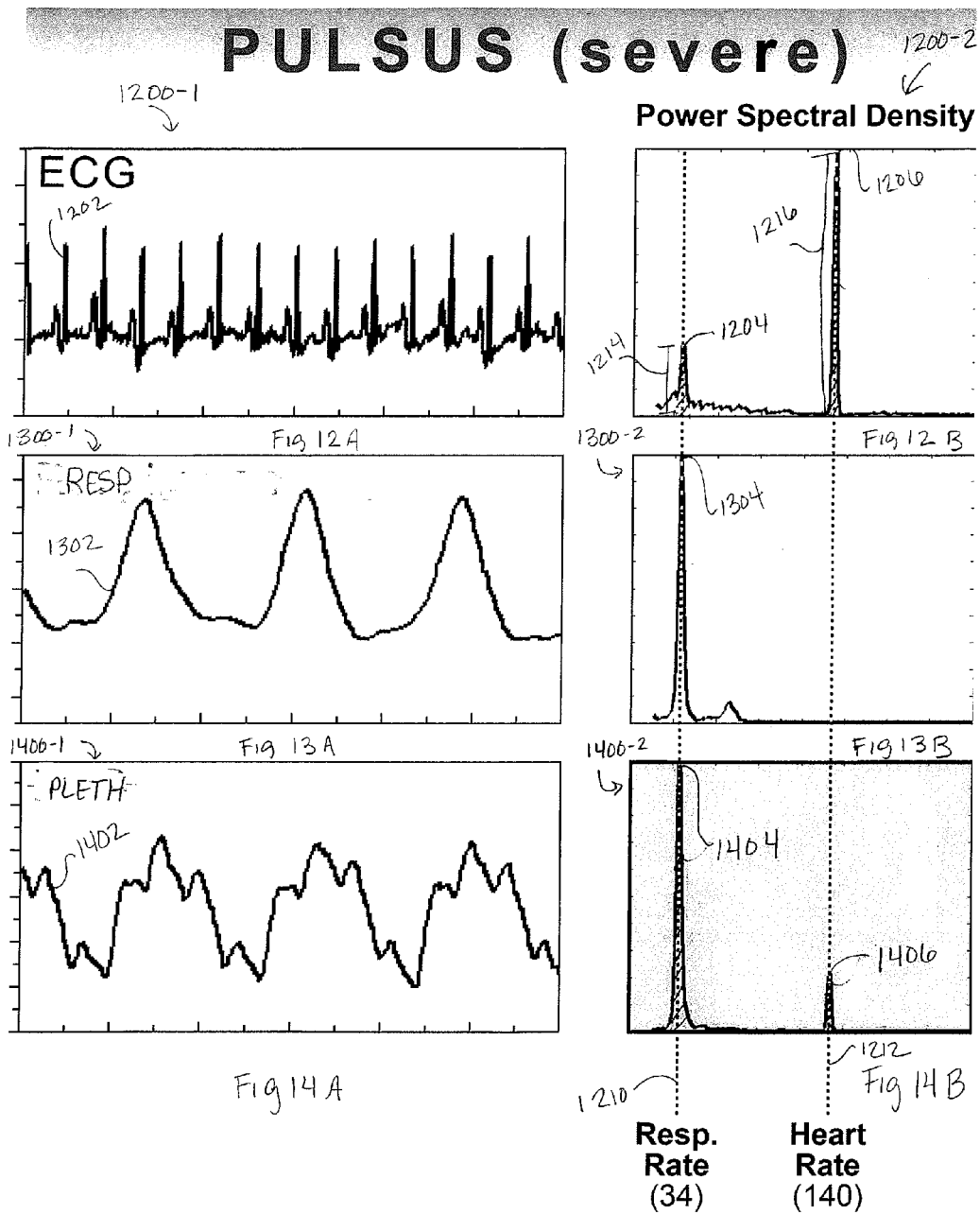

METHOD AND SYSTEM FOR DETECTION OF RESPIRATORY VARIATION IN PLETHYSMOGRAPHIC OXIMETRY

CROSS REFERENCE TO RELATED APPLICATIONS

This is a continuation-in-part of co-pending U.S. patent application Ser. No. 13/404,265, filed Feb. 24, 2012, which is a divisional of U.S. Pat. No. 8,128,569, filed Dec. 5, 2008, which claims priority from U.S. Provisional Patent Application No. 60/992,973, filed on Dec. 6, 2007.

BACKGROUND

Field

A method and system for detection of variations in plethysmographic oximetry.

Background

Pulsus paradoxus is a term referring to a systolic arterial pressure and pulse pressure that weakens abnormally during inspiration. It was first recognized in 1873 when an irregularity of the palpable pulse was observed while the heart sounds indicated that the cardiac rhythm was regular. It was found that the "irregularity" of the pulse resulted from a reduction in left ventricular stroke volume leading to an impalpable pulse during inspiration. Pulsus paradoxus may be symptomatic of various abnormalities including pericardial tamponade, worsening asthma, chronic obstructive pulmonary disease, congestive heart failure, pulmonary edema, chronic dyspnea, obstructive sleep apnea and tension pneumothorax. If left undetected, these disorders may result in deterioration or death of critically ill patients. Thus, early detection is essential.

In a healthy individual, arterial and venous blood pressures vary throughout the respiratory cycle. It is not uncommon to see an increase in blood pressure during expiration followed by a decrease in blood pressure during inspiration. Such fluctuations may occur due to the intrathoracic pressure changes generated during breathing. Although the exact physiology behind pulsus paradoxus may vary depending upon the disease it is symptomatic of, the exaggerated pressure decrease may generally be explained by the interrelationship between the changing intrathoracic pressure during the respiratory cycle and the two ventricular chambers of the heart. During inspiration intrathoracic pressure decreases which augments right heart filling, pulmonary vascular compliance, and right ventricular stroke volume while reducing left heart filling and output.

Pulsus paradoxus may be detected by monitoring changes in blood pressure throughout the respiratory cycle. Under normal conditions, an individual may experience a decrease in arterial blood pressure of less than 10 millimeters mercury (mmHg) during inspiration. An abnormality is identified where this pressure decrease exceeds 10 mmHg. Currently there are a variety of techniques available for detecting this pressure decrease during inspiration.

One such technique for detection of pulsus paradoxus requires gradually deflating a sphygmomanometer (blood pressure cuff) while listening for the onset of Korotkoff sounds (sounds resulting from arterial pressure waves passing through the occluding cuff) during normal respiration. The Korotkoff sounds will first be audible during expiration only, and after further deflation of the cuff, during inspiration as well. If the cuff is deflated more than 10 mmHg between detection of intermittent and constant Korotkoff sounds, pulsus paradoxus is said to be present. This method of detection is problematic for a number of reasons, not the least of which is that automated blood pressure monitoring recording is now standard throughout the health care industry and this technique is incapable of detecting respiratory fluctuations in arterial pressure since only one set of systolic and diastolic pressures are recorded. Even when manual sphygmomanometers are available, the operator has to be alerted to the possibility that pulsus paradoxus could be present and know how to perform the test. In addition, manually-obtained blood pressure values are subjective in that they are reliant upon the operator's ability to listen to the sounds while watching the fluctuations of the gauge. The only record is therefore the operators' hand-written description of a highly subjective test.

A second technique used in detecting pulsus paradoxus is by direct monitoring of arterial pressure with an indwelling intra-arterial catheter. This technique is more accurate than sphygmomanometry in detecting pulsus paradoxus because it results in a permanent recording of the arterial waveform and pressure and thus allows for an objective measurement. Due to its invasive nature, however, it is often painful to the patient and requires a highly trained health care provider.

Infrared photosensors used for pulse oximetry and plethysmography may be utilized for a third technique that may be used for detecting pulsus paradoxus. In this technique, changes in the intensity of an infrared (IR) beam passing through a patient's finger tip, toe, or earlobe are obtained to measure fluctuations in regional blood volume, a correlate of blood pressure. A surface-mounted, non-invasive probe sends an IR beam through the fleshy tissue and receives reflections therefrom. Changes in the amount of blood in the measurement area (i.e., a capillary bed) cause changes in absorption or variation, and such changes vary along with the amount of blood delivered to that tissue. Thus, although not a direct measure of the patient's blood pressure, the plethysmographic signal emulates the waveform contour and magnitude of direct intra-arterial pulse pressure and is typically displayed on a monitor screen along with the electrocardiogram and respiratory excursions. Clinical use of this measurement, called plethysmographic oximetry (PO), has been reported to detect pulsus paradoxus in children with pericardial tamponade and in adults with respiratory distress from obstructive lung disease but these results have not yet been incorporated into devices that would make possible simply applied, non-invasive, real-time detection of pulsus paradoxus.

The above described techniques for detection of pulsus paradoxus are highly subjective, labor intensive and inaccurate (if measured with a blood pressure cuff), or invasive (if done with arterial lines) and therefore, are rarely used. Thus, the ability to detect the ominous condition of pulsus paradoxus requires a high level of suspicion and cumbersome or invasive technology. As a result, pulsus paradoxus and therefore early signs of several life-threatening conditions often go undetected.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

FIG. 2 illustrates a physiologic respiratory wave review of a patient.

FIG. 3 illustrates a pathological wave review of a patient indicative of pulsus paradoxus.

FIG. 9A illustrates an electrocardiogram wave review indicative of pulsus paradoxus.

FIG. 9B illustrates a power spectrum density of the electrocardiogram wave review of FIG. 9A.

FIG. 10A illustrates a respiratory wave review.

FIG. 10B illustrates a power spectrum density of the respiratory wave review of FIG. 10A.

FIG. 11A illustrates a plethysmographic wave review indicative of pulsus paradoxus.

FIG. 11B illustrates a power spectrum density of the plethysmographic wave review of FIG. 11A.

FIG. 12A illustrates an electrocardiogram wave review indicative of pulsus paradoxus.

FIG. 12B illustrates a power spectrum density of the electrocardiogram wave review of FIG. 12A.

FIG. 13A illustrates a respiratory wave review.

FIG. 13B illustrates a power spectrum density of the respiratory wave review of FIG. 13A.

FIG. 14A illustrates a plethysmographic wave review indicative of pulsus paradoxus.

FIG. 14B illustrates a power spectrum density of the plethysmographic wave review of FIG. 14A.

DETAILED DESCRIPTION

Figure 1A:
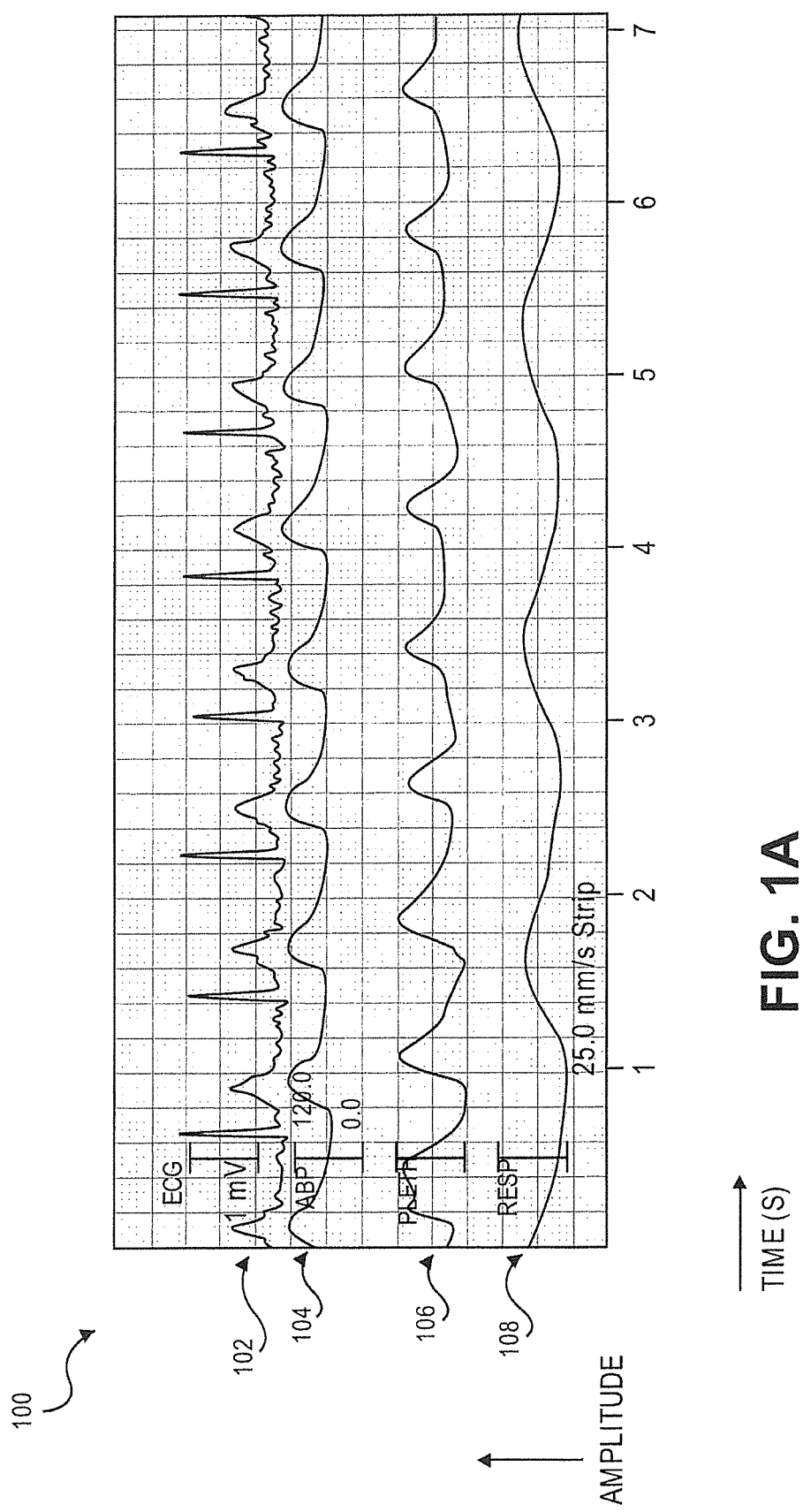
FIG. 1A illustrates simultaneous recordings from a patient of an electrocardiogram wave review (ECG), a blood pressure wave review (ABP), a plethysmographic wave review (PLETH) and a respiratory wave review (RESP).

Automatic and sensitive detection of respiratory variation in cardiac activity may be a major asset in emergency departments, medical and surgical intensive care units (ICU), operating rooms, and hospices since it is especially difficult to determine worsening of many conditions with current manual systems and those focusing on changes in arterial blood pressure alone. Such detection may allow health care physicians to more quickly address and treat conditions such as, for example, chronic apnea and tension pneumothorax. Moreover, an automated system and method as described herein may be useful in nursing homes or hospices where detection of impending respiratory failure may allow families to be notified of important changes in conditions as they occur. Still further, detection of hemodynamic changes that happen consistently in obstructive sleep apnea may improve diagnosis or help avoid expensive diagnostic testing in sleep laboratories. It is thus believed, automated detection of pulsus paradoxus would help to identify and intervene in patient care resulting in thousands of lives saved each year.

In one embodiment, a method for detection of pulsus paradoxus is disclosed. In one aspect, the method includes detection of a pattern consistent with a respiratory cycle of waveforms representing cardiac oscillations to detect an abnormality in the pattern. In one embodiment, a plethysmographic oximeter system may be used to measure and display a respiratory waveform and concurrent waveform representing cardiac oscillations (plethysmograhic oximetry waveform) over a period of time. In this context, a lead from the system may include sensors for monitoring a patient's respiratory activity. The system may further include a lead for monitoring cardiac activities. Still further, leads may include electrocardiogram sensors (ECG) and/or sensors for detecting a pulse rate. The system may display information relating to each of these measurements in a waveform on an interface of the system. These waveforms may then be analyzed and scored by dividing averaged offsets of pulse waves from a base line with average wave amplitudes over a respiratory cycle. A score falling within a particular range indicates an abnormality (e.g. oscillating base of a plethysmographic wave from a baseline).

In another embodiment, a method for detection of pulsus paradoxus includes using spectral density estimation techniques, such as Welch's method, or using Hjorth parameters, to determine a distribution of the frequencies embodied in the power spectrum density plethysmographic waveforms. This approach is based on the insight that the plethysmographic waveform is the sum of one or more periodic waveforms, including pulse and respiration. In a normal plethysmographic waveform, the pulse dominates the overall signal, with respiration only a minor contributor. The presence of pulsus paradoxus will increase the contribution of respiration to the waveform. On a power spectral density plot, the presence of pulsus paradoxus is confirmed when the peak corresponding to the respiration rate approaches or exceeds the peak corresponding to the pulse rate.

FIG. 1A illustrates simultaneous normal ECG 102, ABP 104, PLETH 106 and RESP 108 recordings from a patient. ECG 102, ABP 104, PLETH 106 and RESP 108 include a tracing of consecutive cycles over a period of seven seconds. Components of the recordings illustrated in FIG. 1A will be described in more detail in reference to FIG. 1B.

An electrocardiogram (ECG) records electrical potentials from the heart. Under normal conditions, an electrical stimulus is generated by the sinus node located in the right atrium of the heart. The sinus node is the pacemaker of the heart and begins the process of depolarization of the atrium and ventricle through conduction pathways and generates an electrical stimulus which initiates the heart beat (e.g., 60 to 190 times per minute depending on the age of the patient). The electrical impulse travels from the sinus node to the atria ventricular (AV) node where it stops for a brief period and continues down the conduction pathways via the bundle of His into the ventricles. Accordingly, the right and left atria are depolarized first followed by depolarization of the right and left ventricle. As the electrical impulse moves through the conduction system, the heart contracts. Each contraction represents one heart beat.

Figure 1B:
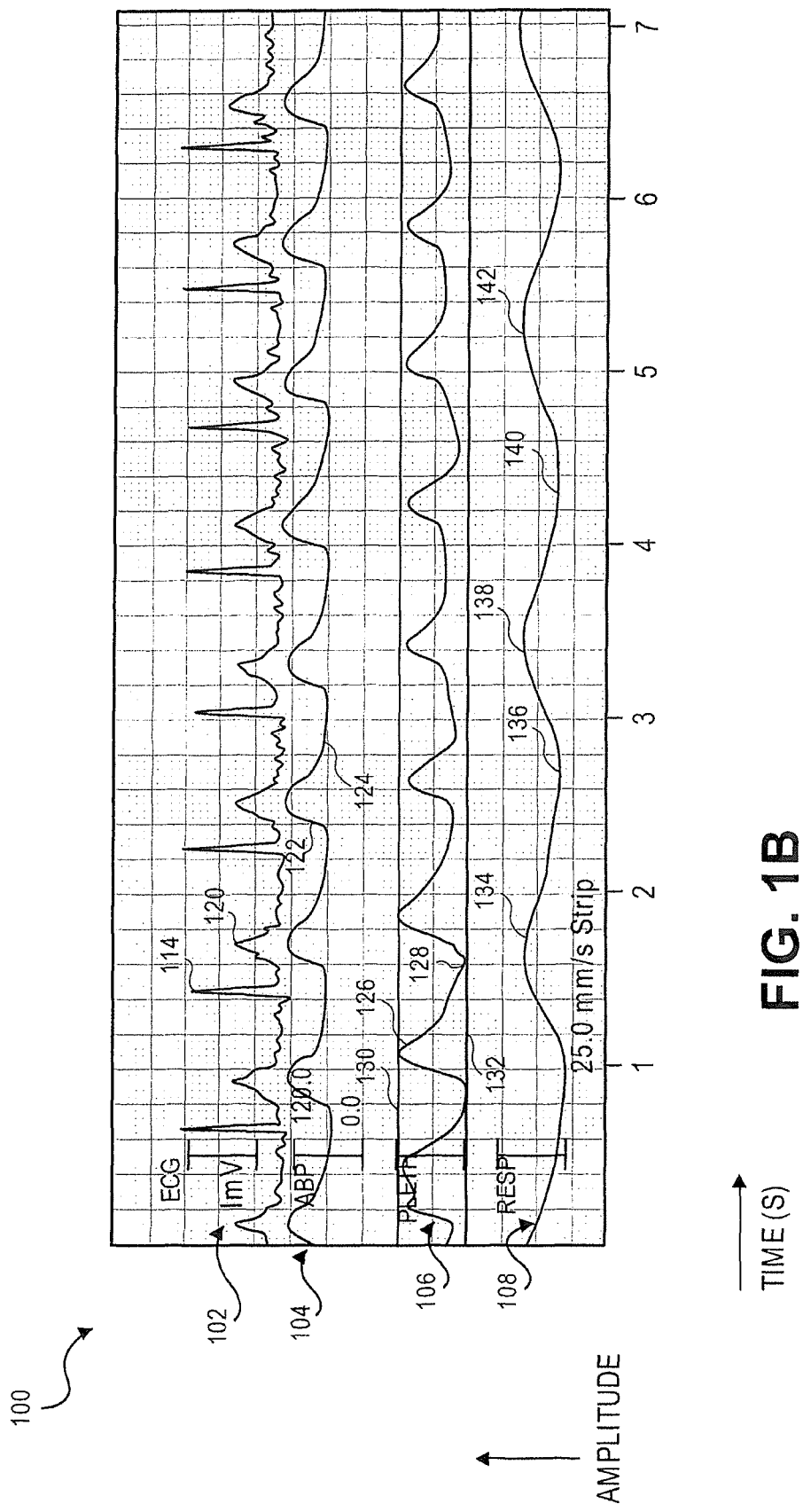
FIG. 1B illustrates the simultaneous recordings of FIG. 1A.

In FIG. 1B, the large vertical spike of ECG 102 is R wave 114 which represents depolarization of ventricles. Each R wave 114 is followed by contraction and pumping of blood. R wave 114 is used as a signal from which other signals are identified. The lower amplitude spike following R wave 114 is T wave 120. T wave 120 represents repolarization of cardiac muscle which then prepares for the next signal from the sinus node.

Each ventricular contraction produces an arterial waveform ABP 104 which can be seen to follow R wave 114 due to the time delay following depolarization and the time for blood to get to the peripheral recording site. ABP 104 is a recording of the arterial pressure. The recording utilizes a cannula inserted into an artery which is in turn transduced into a scaled electrical signal. The height or amplitude is scaled in mmHg. ABP 104 illustrates the ABP in the radial artery caused by the pressure generated by contraction of the heart's left ventricle. ABP includes a systolic pressure defined as the peak pressure in the arteries during the cardiac cycle and a diastolic pressure defined as the lowest pressure at the resting phase of the cardiac cycle. ABP waveform 104 includes "up" 122 and "down" 124 fluctuations of the arterial blood pressure resulting from the pulsatile nature of the cardiac output. The pulse pressure is determined by the interaction of the stroke volume versus the volume and elasticity of the major arteries. Normal ABP ranges for adult humans are systolic between 90 mmHg and 135 mmHg and diastolic between 50 mmHg and 90 mmHg.

Referring to PLETH waveform 106, the waveform represents a patient having a steady unchanging pulse with a heart rate of about 80 beats per minute. PLETH waveform 106 may be recorded from a fingertip device utilized to determine an index of tissue oxygenation. In this aspect, each wave represents a pressure exerted when the heart contracts. For a typical healthy adult human a normal PLETH waveform 106 is about 120 mmHg/60 mmHg. Horizontal borderlines 130, 132 are illustrated along waveform 106 to emphasize the regularity of the waves. In particular, peak borderline 130 extends along an upper limit defined by wave peaks 126 of PLETH waveform 106 and baseline 132 extends along a lower limit along wave bases 128 of PLETH waveform 106. It can be seen that the waves of PLETH waveform 106 have a regular height or amplitude (i.e., distance from peak 126 to baseline 132). In addition, each wave base 128 is substantially aligned with baseline 132 such that no significant baseline oscillations are present.

Referring to RESP waveform 108, the waveform represents respiratory excursions where "up" waves 134, 138, 142 represent inspiration and "down" waves 136, 140 represent expiration. RESP waveform 108 may be obtained from impedance plethysmography using standard ECG electrodes. Impedance plethysmography is a non-quantitative signal arising from movement of ECG sensors placed on the patient's thorax as the thorax rises and falls. RESP waveform 108 is shown having a regular respiratory tracing and may have a rate of approximately 16 to 30 breaths per minute. Wave peaks representing inspiration may be used to define each respiratory cycle. For example, a respiratory cycle may be defined by peaks 134 and 138 while another cycle may be defined by peaks 138 and 142.

It can be seen from FIGS. 1A and 1B that ECG 102, ABP 104 and PLETH 106 waveforms have the same frequency though it is noted that there is a physiologic offset such that the ABP signal occurs after ECG and the PLETH signal occurs after ABP. In a normal healthy human, there is a correlation in the ECG, ABP and PLETH waveforms and at most a subtle relationship between PLETH and RESP.

FIG. 2 illustrates a physiologic respiratory wave review of a patient. RESP wave review 200 shows an exemplary embodiment of a physiologic wave review for purposes of illustrating a measurement of an average respiratory cycle distance for use in detection of an abnormality in a pattern representing cardiac oscillations. In this aspect, a RESP waveform 204 of RESP wave review 200 includes peaks 212, 214, 216, 218 representing inspiration. A baseline 202 from which an amplitude of peaks 212, 214, 216, 218 may be determined is further shown. An average respiratory cycle distance may be determined by first measuring a distance from one peak to the next. An average distance, D, may then be determined by averaging the distances of at least two consecutive respiratory cycles. For example, a distance, $d^1$, between peaks 212 and 214 may be measured to identify a first cycle 206 while a distance $d^2$ between peaks 214 and 216 may be measured to identify a second cycle 208. An average is taken of distance $d^1$ and $d^2$ to determine average respiratory cycle distance D. Still further, distance $d^3$ (between peaks 216 and 218) of a third respiratory cycle 210 may be measured and averaged with distances $d^1$ and $d^2$ to arrive at average respiratory cycle distance D.

FIG. 3 illustrates a wave review with variation in a PLETH waveform for a patient with a regular sinus rhythm. In particular, it can be seen from FIG. 3 that bases of waves of PLETH wave review 300 are offset (i.e. oscillate) from a baseline 305. These oscillations may be analyzed to determine whether they are indicative of pulsus paradoxus by dividing the waves into groups, or cycles, which correspond to an average respiratory cycle distance, D, for the patient as described above. For the purpose of illustrating this concept, an average respiratory cycle D (e.g. average distance of cycles 206, 208, 210) as described above in reference to FIG. 2 is used to identify wave cycles 320, 330 of FIG. 3. It is recognized, however, that RESP wave review 200 and PLETH wave review 300 are not drawn to scale. For example, cycle 320 is identified by measuring average respiratory cycle D from the beginning of a blood pressure increase along baseline 305. Cycle 330 then extends a distance D from an end of cycle 320. It can be seen from FIG. 3 that each cycle 320, 330 includes about eight wave peaks 350 and thus approximately eight waves. Once a cycle is determined, a height, h, is measured from each wave base 340 to baseline 305. An average height, H, is then determined using each height, h, measured from wave bases 340 to baseline 305. For example, in cycle 320 an average height H may be calculated by adding each of heights $h^1$, $h^2$, $h^3$, $h^4$, $h^5$, $h^6$, $h^7$, $h^8$ together and dividing by eight. Average height H is then used to form a triangle as shown in FIG. 3 having a height H, a base D and hypotenuse 360 representative of a best-fit line to wave bases 340. An average wave amplitude, A, may then be determined for each cycle 320, 330 by determining an amplitude, a, of each wave from hypotenuse 360 to a wave peak 350 and averaging the amplitudes. For example, in cycle 320 an average amplitude A may be calculated by adding each amplitude $a^1$, $a^2$, $a^3$, $a^4$, $a^5$, $a^6$, $a^7$, $a^8$ from hypotenuse 360 to a wave peak 350 and averaging the amplitudes. The above described analysis may be repeated for cycle 330. A value (i.e., score) for cycles 320 and 330 may then be determined according to the formula H/A wherein H represents the average offset from the baseline of the waves and A represents average amplitude for cycle. Using the above analysis, the degree of wave oscillations within each cycle may be evaluated to determine whether they are indicative of pulsus paradoxus.

For example, in one embodiment illustrated in FIG. 3, average distance, D, may be approximately 3.5 centimeters (cm) such that cycle 320 is made up of waves within a region of baseline 305 3.5 cm in length. An average height, H, of cycle 320 may be approximately 0.356 cm (i.e., $h^1$=0.5 cm, $h^2$=0.5 cm, $h^3$=0.4 cm, $h^4$=0.3 cm, $h^5$=0.3 cm, $h^6$=0.3 cm, $h^{7=0.25}$ cm, $h^8$=0.3 cm) and average amplitude A may be approximately 1.113 cm (i.e., $a^1$=0.7 cm, $a^2$=1.1 cm, $a^3$=1.3 cm, $a^4$=1.35 cm, $a^5$=1.25 cm, $a^6$=1.2 cm, $a^7$=1.1 cm, $a^8$=0.9 cm) resulting in a score of 0.32 (0.356 cm/1.113 cm). In one embodiment, an alarm 660 (see FIG. 6) may be triggered by a score (calculated, for example, as described above, offset over amplitude) falling within a range indicative of pulsus paradoxus (i.e., pressure decrease greater than 10 mmHg). Thus, in one embodiment a value indicative of pulsus paradoxus may be 0.32. In one aspect, a range indicative of pulsus paradoxus may be, for example, a score from about 0.3 to about 2.5 and still further a score from about 1.6 to about 2.5 may be indicative of pulsus paradoxus. It is believed a score below 0.3 is within the normal range. Still further, alarm 660 may be triggered by a score indicative of a variety of cardiopulmonary disorders, often in combination. In this aspect, the alarm may be triggered by a score in a range of, for example, about 0.3 to about 1.6.

As described herein, variations in a plethysmographic signal as previously described may indicate pulsus paradoxus. It is further contemplated, however, that each of the wave reviews illustrated in FIGS. 1A and 1B (ECG, ABP, RESP), should be considered in determining whether or not variations in a patient's plethysmographic signal are indicative of pulsus paradoxus or some other condition. For example, where plethysmographic signal variations are detected in a patient with an irregular sinus rhythm, the variations in the plethysmographic signal may correspond to the irregular sinus rhythm thereby suggesting an arrhythmic, rather than respiratory related, reason for the variations.

Figure 4:
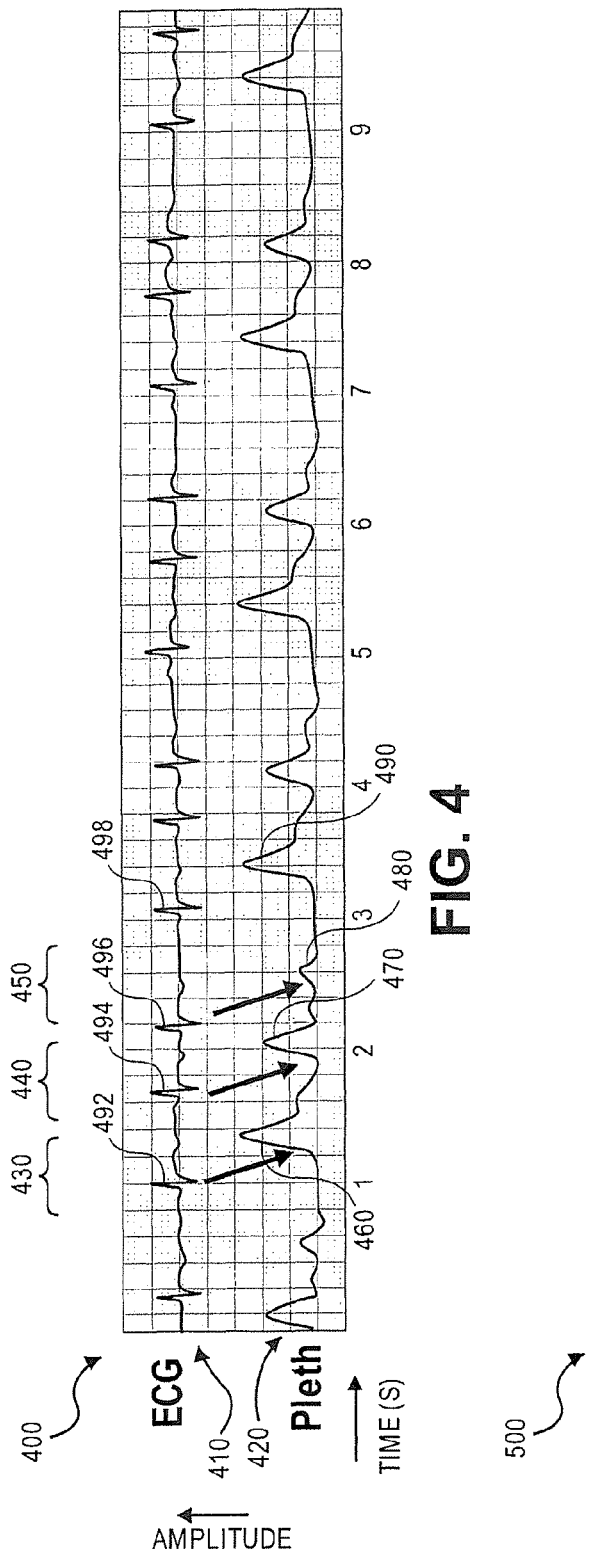
FIG. 4 illustrates a pathological wave review of a patient indicative of changes in stroke volume resulting from premature atrial beats.

FIG. 4 illustrates one such pathological wave review of a patient indicative of changes in stroke volume resulting from premature atrial beats. The term "stroke volume" as used herein refers to the volume of blood ejected from a ventricle with each beat of the heart. FIG. 4 shows wave review 400 including an ECG waveform 410 and PLETH waveform 420 of a patient. In this embodiment, an abnormality is detected based upon the frequency of ECG waveform 410 complexes with respect to PLETH waveform 420 over several consecutive cycles 430, 440, 450. In particular, in review 400, PLETH waveform 420 illustrates three repetitive plethysmographic waves 460, 470, 480 corresponding to cycles 430, 440 and 450 of ECG waveform 410. Waves 460, 470, 480 represent a late beat 460 following a pause, a normal beat 470 and a premature beat 480. In particular, beat 460 is seen having a large amplitude due to the extra fill time resulting from a pause preceding the beat. In the case of premature beat 480, the resulting pulse has a much lower amplitude than normal because the heart does not have an adequate fill time. This pattern of late, normal and premature beats then continues such that the next beat 490 following beat 480 has an adequate fill time and thus appears much like beat 460. The magnitude of these waves matches the expected variation in stroke volume illustrated by ECG R waves 492, 494, 496, 498. Accordingly, upon viewing this pattern, a health care provider will recognize that the variability in PLETH waveform 420 corresponds to the pattern of heart beats shown in ECG waveform 410 and should therefore dismiss concerns regarding pulsus paradoxus.

Figure 5:
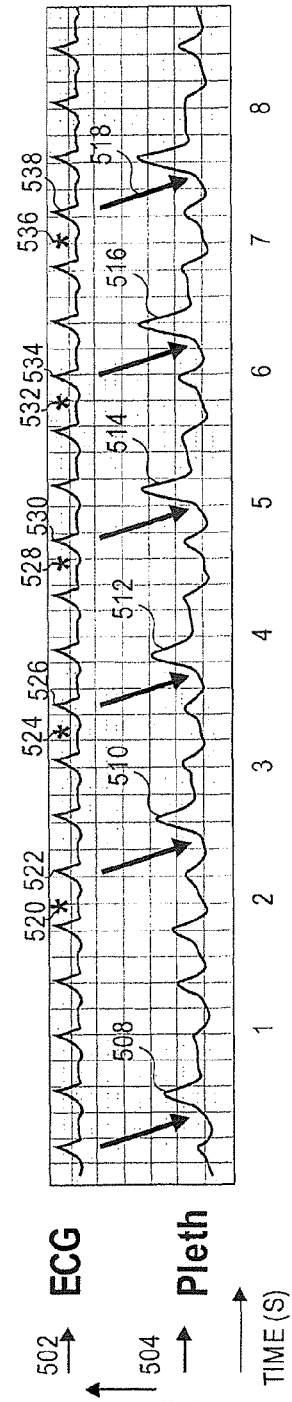
FIG. 5 illustrates a pathological wave review of the patient of FIG. 4 indicative of wide complex tachycardia.

FIG. 5 illustrates a wave review comparison of an ECG waveform and PLETH waveform of the patient from FIG. 4. Wave review 500 shows ECG 502 and PLETH 504 waveforms. ECG waveform 502 demonstrates a wide complex tachycardia, rate 140, without obvious P waves. P waves represent depolarization of the atria. PLETH waveform 504 depicts periodic large pulses 508, 510, 512, 514, 516, 518 resulting from intermittent sequential atrio-ventricular contractions, diagnostic of ventricular contractions with atrio-ventricular dissociation. The slower atrial rhythm is not obvious on ECG waveform 502 but the presence of P waves can be discerned by subtle flattening of T waves 520, 524, 528, 532, 536 preceding each of the R waves 522, 526, 530, 534, 538, respectively, responsible for the larger plethysmographic excursions (pulses) 508, 510, 512, 514, 516, 518 of PLETH waveform 504. In this aspect, a health care provide viewing these results can see that the variability in PLETH waveform 504 corresponds to the pattern of heart beats depicted by ECG waveform 502 and therefore the variability is heart beat by heart beat rather than respiratory thus eliminating pulsus paradoxus as a potential cause of the variability.

It is further appreciated that Traube-Hering-Mayer waves may further be responsible for variations in a plethysmographic waveform. Traube-Hering-Mayer waves are oscillations that have been measured in association with blood pressure, heart rate, cardiac contractility, pulmonary blood flow, cerebral blood flow and movement of the cerebrospinal fluid, and peripheral blood flow including venous volume and thermal regulation. The waves exhibit a rate typically slightly less than and independent of respiration and resemble the primary respiratory mechanism. Thus, where, for example, a fluctuation in pulse pressure with the frequency of respiration persists after respiration has been arrested, Traube-Hering-Mayer waves, in addition to respiratory causes, should be considered in evaluating the cause of the fluctuation.

Figure 6:
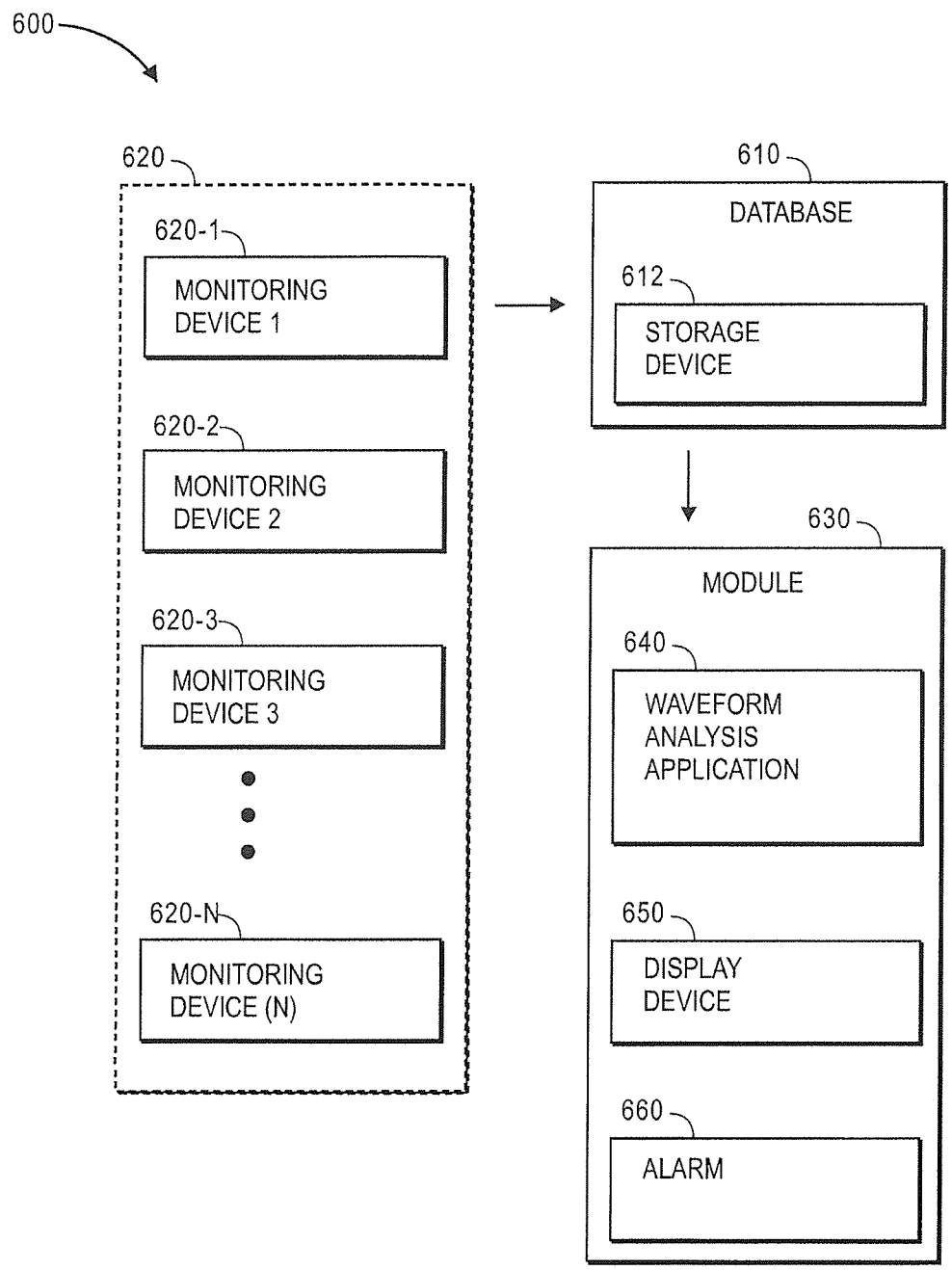
FIG. 6 illustrates a system for detecting pulsus paradoxus.

FIG. 6 illustrates a system 600 detecting waveform patterns and detecting an abnormality in the pattern. In this aspect, system 600 includes a database 610 to receive and store data representing a physiological condition of the patient over a period of time, wherein the data comprises data corresponding to respiratory activity and cardiac oscillations. The data corresponding to the respiratory activity and cardiac oscillations may be recorded and stored in a storage device 612 of database 610. System 600 may include a patient monitoring device 620 to generate data representing a physiological condition of a patient over time for storage in database 610. In an alternative embodiment, system 600 may include any number of patient monitoring devices 620 connected to a patient to measure, for example, heart rate, blood volume, systolic and diastolic blood pressure, and/or plethysmographic oxygen saturation. In this aspect, patient monitoring devices 620 include, monitoring devices 620-1 through 620-N. In one embodiment, patient monitoring device 620 may be a plethysmographic oximeter or any similar device capable of measuring and displaying respiratory and/or cardiac activity. In an alternative embodiment, patient monitoring device 620 may include a plethysmographic oximeter and an ECG (e.g., monitoring device (620-1) is a plethysmographic oximeter and monitoring device (620-2) is an ECG). Data generated by patient monitoring devices 620 may be in various formats. In one embodiment, the data may be in text format. In an alternative embodiment, the data may be in a waveform format suitable for providing a waveform image.

System 600 may include module 630 to receive and process data generated by monitoring devices 620. In this aspect, module 630 may include a waveform analysis application 640 running on module 630. In one embodiment, waveform analysis application 640 converts waveform data into a quantifiable format for measuring changes in waveform characteristics. In this aspect, portions of the waveform data are examined by waveform analysis application 640 to extract features or patterns that are pertinent to analysis of the waveform data. There are a number of techniques that may be used to extract pertinent information from the waveform data. For example, pertinent information from the waveform data can be extracted by determining frequency and amplitude of the waveforms at various points. The waveform data can also be analyzed by examining at least two cycles of the waveform in conjunction with a second waveform. This may be accomplished by capturing a segment of the waveform data of each waveform and defining a single cycle and analyzing the captured segment perhaps by applying a suitable algorithm, such as pattern recognition algorithm or transform algorithm. For example, waveform analysis application 640 may be configured to extract a pattern consistent with a respiratory cycle of a waveform representing cardiac oscillations illustrated in FIG. 3 by examining relevant data according to the above processes. In addition, waveform analysis application 640 may be configured to convert the waveform data (e.g. PLETH waveform data described in reference to FIG. 7) into a power spectrum wave review that can be analyzed by module 630 or manually.

In one embodiment, waveform analysis application 640 may further be configured to monitor the waveform patterns and extract abnormal patterns (e.g. wave oscillations in cardiac waveforms) as described in reference to FIG. 3 and FIG. 7 below. When an abnormality in, for example, a plethysmographic waveform is found for several consecutive respiratory cycles, storage of the two signals (respiratory and cardiac) is begun. The signals are then quantified and compared to determine a score as previously discussed. If the score is within a range indicative of an abnormality such as pulsus paradoxus, alarm 660 further included in module 630 is activated to alert the care provider. Alarm 660 may be any type of alarm capable of alerting a care provider of the presence of pulsus paradoxus, for example, an audio alarm or a visual alarm. Alternatively or in addition to, information pertinent to the waveform data may be extracted manually. This may be accomplished by, for example, a person who is trained to recognize pulsus paradoxus by manually examining the physiological data (including waveform data) displayed on a display device 650 (i.e. interface) of module 630.

Figure 7:
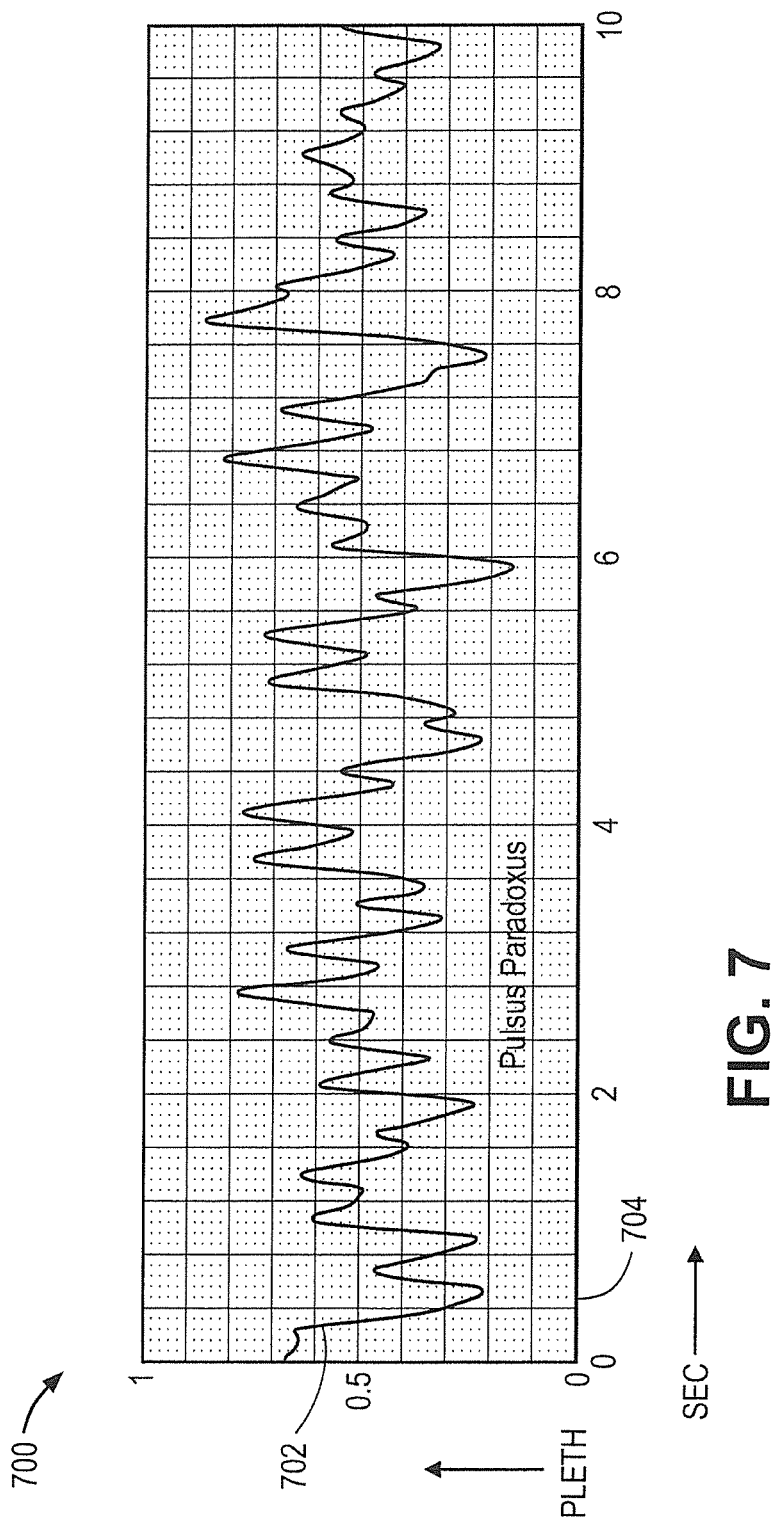
FIG. 7 illustrates a plethysmographic wave review indicative of pulsus paradoxus.

FIG. 7 illustrates a plethysmographic (PLETH) wave review indicative of pulsus paradoxus. In particular, as can be seen from PLETH wave review 700, a base of PLETH wave 702 oscillates from baseline 704. The presence of pulsus paradoxus can be confirmed from PLETH wave review 700 by measuring an average offset of the wave bases of the waveform from baseline 704 and an average amplitude of the waveform peaks as previously discussed.

Figure 8:
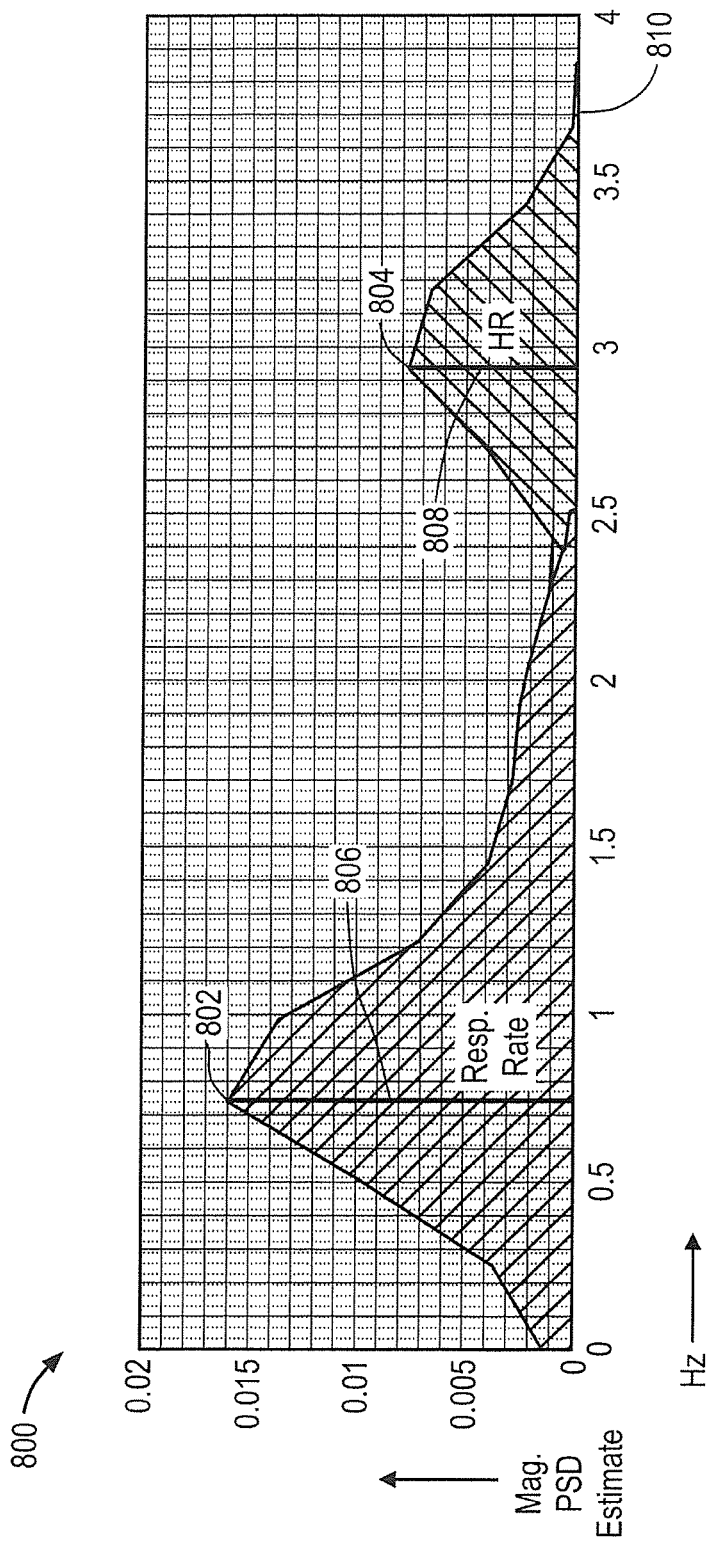
FIG. 8 illustrates a power spectrum density of the plethysmographic wave review of FIG. 7.

Alternatively, the presence of pulsus paradoxus can be confirmed using a power spectrum density (PSD) plot of PLETH wave review 700. A PSD plot of PLETH wave review 700 is illustrated in FIG. 8. PSD 800 of PLETH wave review 700 can be determined using a number of approaches, including Welch's method, or by use of Hjorth parameters. PSD 800 can be generated using, for example, the algorithm described in Deshame, A., False Arrhythmia Alarm Suppression Using ECG, ABP, and Photoplethysmogram, *Massachusetts Institute of Technology*, September 2009, which is incorporated herein by reference. PSD 800 can also be generated using, for example, Welch's method, described in Welch, P. D. "The Use of Fast Fourier Transform for the Estimation of Power Spectra: A Method Based on Time Averaging Over Short, Modified Periodograms", *IEEE Transactions on Audio Electroacoustics*, 15:2, 70-73. June 1967, which is incorporated herein by reference.

As can be seen from FIG. 8, PSD 800 includes two dominant frequencies determined from data corresponding to wave review 700. In particular, PSD 800 includes a respiratory wave peak 802 (RWP) indicative of a respiratory rate and heart wave peak 804 (HWP) indicative of a heart rate. RWP 802 generally corresponds to a respiratory rate of from about 6-40 breaths per minute. HWP 804 generally corresponds to a heart rate of about 40-160 beats per minute. Pulsus paradoxus can be determined by comparing a height of RWP 802 and a height of HWP 804. Representatively, height 806 of RWP 802 may be measured from baseline 810 and height 808 of HWP 804 may be measured from baseline 810. In some embodiment, when a proportion of RWP height 806 to HWP height 808 is within a predetermined range, pulsus paradoxus is present. For example, in some embodiments, when RWP height/HWP height is from about 0.6 to about 3, pulsus paradoxus is determined to be present. In still further embodiments, the presence of pulsus paradoxus can be determined based on a difference between RWP height 806 and HWP height 808. For example, pulsus paradoxus may be confirmed where RWP height 806 is different than HWP height 808, for example, greater than or less than HWP height 808.

In still further embodiments, pulsus paradoxus may be determined based upon a comparison of an area under the curve (illustrated in diagonal lines) corresponding to RWP 802 and the area under the curve (illustrated in diagonal lines) corresponding to HWP 804. For example, when the area under RWP 802 is greater than or equal to the area under HWP 804, pulsus paradoxus is present.

In other embodiments, pulsus paradoxus may be determined and/or confirmed using a multichannel analysis. In particular, PSD plots corresponding to an electrocardiogram (ECG) waveform, a respiration (RESP) waveform and a plethysmographic (PLETH) waveform can be compared and/or analyzed alone or in combination to determine and/or confirm the presence of pulsus paradoxus.

Representatively, FIGS. 9A-11B illustrate PSD plots corresponding to ECG, RESP and PLETH channels for a sample taken from the channels at the same time, namely at the onset of pulsus paradoxus. FIGS. 12A-14B illustrate PSD plots corresponding to ECG, RESP and PLETH channels for a sample taken from the channels at a time later than that illustrated in FIGS. 9A-11B, namely during the occurrence of severe pulsus paradoxus.

Referring to the figures in more detail, FIG. 9A illustrates an ECG wave review 900-1 of an ECG waveform 902. FIG. 9B illustrates an ECG PSD 900-2, which corresponds to ECG wave review 900-1. ECG PSD 900-2 includes a respiratory wave peak 904 (RWP) indicative of a respiratory rate and a heart wave peak 906 (HWP) indicative of a heart rate.

FIG. 10A illustrates a RESP wave review 1000-1 of a RESP waveform 1002 for the same sample time illustrated in FIGS. 9A-9B. FIG. 10B illustrates a RESP PSD 1000-2, which corresponds to RESP wave review 1000-1. RESP PSD 1000-2 includes a respiratory wave peak 1004 (RWP) indicative of a respiratory rate, but not a heart wave peak since RESP wave review 1000-1 corresponds only to respiratory rate data obtained at the time the sample is taken.

FIG. 11A illustrates a PLETH wave review 1100-1 of a PLETH waveform 1102 for the same sample time illustrated in FIGS. 9A-9B and 10A-10B. FIG. 11B illustrates PLETH PSD 1100-2, which corresponds to PLETH wave review 1100-1. PLETH PSD 1100-2 includes respiratory wave peak 1104 (RWP) indicative of a respiratory rate and heart wave peak 1106 (HWP) indicative of a heart rate.

Since ECG PSD 900-2, RESP PSD 1000-2 and PLETH PSD 1100-2 all correspond to data obtained from a patient at the same time, they can be aligned as shown for the purpose of comparing the respiratory wave peaks and heart wave peaks from each channel to determine and/or confirm the presence of pulsus paradoxus. The dotted vertical line 910 illustrates where RWP 904, 1004 and 1104 line up and dotted vertical line 912 illustrates where HWP 906 and 1106 line up.

In one embodiment, ECG PSD 900-2, RESP PSD 1000-2 and PLETH PSD 1100-2 are used in combination to determine pulsus paradoxus. In particular, the presence of RESP PSD 1000-2 can be used to confirm the identity of RWP 904 in ECG PSD 900-2 and RWP 1104 in PLETH PSD 1100-2. In other words, from RESP PSD 1000-2, RWP 1004 can be identified and confirmed. RWP 1004 can then be compared to the peaks found in ECG PSD 900-2 and PLETH 1100-2 to confirm that the respiratory peaks are RWP 904 and RWP 1104, respectively. In addition, the HWP 906 found in ECG PSD 900-2 can be used to identify and/or confirm the HWP 1106 found in PLETH PSD 1100-2. It is contemplated that using all three channels, namely ECG, RESP and PLETH, allows for verification or confirmation of the determination of pulsus paradoxus from PLETH PSD 1100-2. Such additional steps are, however, optional.

In addition, as can be seen from ECG PSD 900-2, both a RWP 904 and HWP 906 are present. Thus, it is further contemplated that, in some embodiments, pulsus paradoxus can be determined directly from ECG PSD 900-2 or PLETH PSD 1100-2. For example, similar to the algorithm discussed in reference to PSD 800 described in FIG. 8, a height 914 of RWP 904 from the baseline and a height 916 of HWP 906 from the baseline may be measured and compared to determine the presence of pulsus paradoxus. Representatively, when a proportion of the height 914 of RWP 904 to the height 916 of HWP 906 is within a predetermined range, pulsus paradoxus is present. For example, in some embodiments, when RWP height/HWP height is from about 0.6 to about 3, pulsus paradoxus is determined to be present. In still further embodiments, the presence of pulsus paradoxus can be determined based on a difference between the height 914 of RWP 904 and the height 916 of HWP 906. For example, pulsus paradoxus may be confirmed where the height 914 of RWP 904 is different than the height 916 of HWP 906, for example, greater than or less than the height 916 of HWP 906. Pulsus paradoxus may be determined from PLETH PSD 1100-2 as previously discussed in reference to PSD 800 described in FIG. 8.

In still further embodiments, an area under the curves forming RWP 904 and HWP 906 or RWP 1104 and HWP 1106 can be compared to determine pulsus paradoxus. For example, when the area under RWP 904 (illustrated in diagonal lines) is greater than or equal to the area under HWP 906 (illustrated in diagonal lines), pulsus paradoxus is determined to be present. Such a determination with respect to ECG PSD 900-2 can be confirmed and/or verified using PLETH PSD 1100-2. Representatively, when the area under RWP 1104 (illustrated in diagonal lines) is greater than or equal to the area under HWP 1106 (illustrated in diagonal lines), pulsus paradoxus is determined and/or confirmed to be present. Alternatively, the area under the curves shown in PLETH PSD 1100-2 or ECG PSD 900-2 can be analyzed alone to determine the presence of pulsus paradoxus.

The area under the curves may be determined by, for example, dropping lines from each shoulder of the dominant peak to the baseline and then the entire area measured. Alternatively, the area under the curve may be measured using pre-determined "windows" for respiratory rates and pulse rates (e.g., from 6-40 for resp, and 40-160 for heart rate).

Returning to FIGS. 12A-14B, FIGS. 12A-14B illustrate PSD plots corresponding to ECG, RESP and PLETH channels for a sample taken during the occurrence of severe pulsus paradoxus.

FIG. 12A illustrates an ECG wave review 1200-1 of an ECG waveform 1202. FIG. 12B illustrates an ECG PSD 1200-2, which corresponds to ECG wave review 1200-1. ECG PSD 1200-2 includes a respiratory wave peak 1204 (RWP) indicative of a respiratory rate and a heart wave peak 1206 (HWP) indicative of a heart rate.

FIG. 13A illustrates a RESP wave review 1300-1 of a RESP waveform 1302 for the same sample time illustrated in FIGS. 12A-12B. FIG. 13B illustrates a RESP PSD 1300-2, which corresponds to RESP wave review 1300-1. RESP PSD 1300-2 includes a respiratory wave peak 1304 (RWP) indicative of a respiratory rate, but not a heart wave peak since RESP wave review 1300-1 corresponds only to respiratory rate data obtained at the time the sample is taken.

FIG. 14A illustrates a PLETH wave review 1400-1 of a PLETH waveform 1402 for the same sample time illustrated in FIGS. 12A-12B and 13A-13B. FIG. 14B illustrates PLETH PSD 1400-2, which corresponds to PLETH wave review 1400-1. PLETH PSD 1400-2 includes respiratory wave peak 1404 (RWP) indicative of a respiratory rate and heart wave peak 1406 (HWP) indicative of a heart rate.

Since ECG PSD 1200-2, RESP PSD 1300-2 and PLETH PSD 1400-2 all correspond to data obtained from a patient at the same time, they can be aligned as shown for the purpose of comparing the respiratory wave peaks and heart wave peaks from each channel to determine and/or confirm the presence of pulsus paradoxus. The dotted vertical line 1210 illustrates where RWP 1204, 1304 and 1404 line up and dotted vertical line 1212 illustrates where HWP 1206 and 1406 line up.

In one embodiment, ECG PSD 1200-2, RESP PSD 1300-2 and PLETH PSD 1400-2 are used in combination to determine pulsus paradoxus. In particular, the presence of RESP PSD 1300-2 can be used to confirm the identity of RWP 1204 in ECG PSD 1200-2 and RWP 1404 in PLETH PSD 1400-2. In other words, from RESP PSD 1300-2, RWP 1304 can be identified and confirmed. RWP 1304 can then be compared to the peaks found in ECG PSD 1200-2 and PLETH 1400-2 to confirm that the respiratory peaks are RWP 1204 and RWP 1404, respectively. In addition, the HWP 1206 found in ECG PSD 1200-2 can be used to identify and/or confirm the HWP 1406 found in PLETH PSD 1400-2. It is contemplated that using all three channels, namely ECG, RESP and PLETH, allows for verification or confirmation of the determination of pulsus paradoxus from PLETH PSD 1400-2. Such additional steps are, however, optional.

In addition, as can be seen from ECG PSD 1200-2, both a RWP 1204 and HWP 1206 are present. Thus, it is further contemplated that, in some embodiments, pulsus paradoxus can be determined directly from ECG PSD 1200-2. For example, similar to the algorithm discussed in reference to ECG PSD 900-2 illustrated in FIG. 9B, a height 1214 of RWP 1204 from the baseline and a height 1216 of HWP 1206 from the baseline may be measured and compared to determine the presence of pulsus paradoxus. Representatively, when a proportion of the height 1214 of RWP 1204 to the height 1216 of HWP 1206 is within a predetermined range, pulsus paradoxus is present. For example, in some embodiments, when RWP height/HWP height is from about 0.6 to about 3, pulsus paradoxus is determined to be present. In still further embodiments, the presence of pulsus paradoxus can be determined based on a difference between the height 1214 of RWP 1204 and the height 1216 of HWP 1206. For example, pulsus paradoxus may be confirmed where the height 1214 of RWP 1204 is different than the height 1216 of HWP 1206, for example, greater than or less than the height 1216 of HWP 1206. Pulsus paradoxus may be determined from PLETH PSD 1400-2 in a similar manner to that described in reference to PSD 800 described in FIG. 8.

In still further embodiments, an area under the curves forming RWP 1204 and HWP 1206 or RWP 1404 and HWP 1406 can be compared to determine pulsus paradoxus. For example, when the area under RWP 1204 (illustrated in diagonal lines) is greater than or equal to the area under HWP 1206 (illustrated in diagonal lines), pulsus paradoxus is determined to be present. Similarly, when the area under RWP 1404 (illustrated in diagonal lines) is greater than or equal to the area under HWP 1406 (illustrated in diagonal lines), pulsus paradoxus is determined to be present. It is noted, however, that an ECG PSD may be less influenced by a respiratory rate of the patient than a PLETH PSD, therefore in the case of any inconsistencies between a pulsus paradoxus determination using ECG PSD and PLETH PSD, the determination based on PLETH PSD should be relied upon. Thus, an analysis of ECG PSD 1200-2 and PLETH PSD 1400-2, alone or in combination, can be used to detect, confirm and/or verify the presence of pulsus paradoxus.

Any one or more of the above algorithms for determining pulsus paradoxus may be implemented by system 600 previously described in reference to FIG. 6. Representatively, monitoring devices 620 may generate data corresponding to any of the previously discussed RESP, ECG and PLETH waveforms and module 630 may receive and process the data, e.g. compare RWP and HWP heights or areas under the RWP and HWP curves to detect the presence of pulsus paradoxus. Any one or more of wave reviews 900-1, 1000-1, 1100-1, 1200-1, 1300-1 and 1400-1 and PSDs 900-2, 1000-2, 1100-2, 1200-2, 1300-2 and 1400-2 may further be displayed by display device 650 as shown in FIGS. 9A-14B to facilitate and/or confirm pulsus paradoxus detection visually. In addition, when pulsus paradoxus is determined using any one or more of the above algorithms, an alarm, such as alarm 660 (see FIG. 6) may be automatically activated by system 600. The alarm may be an audio alarm or a visual alarm, such as a plot of a plethysmograph, a PSD plot, a plot of how many episodes of pulsus paradoxus occurred in the last 24 hours, or even a text message sent to mobile device, pager, or computer screen.

In the preceding detailed description, specific embodiments are described. It will, however, be evident that various modifications and changes may be made thereto without departing from the broader spirit and scope of the claims. The specification and drawings are, accordingly, is to be regarded in an illustrative rather than restrictive sense.

What is claimed is:

1. A method comprising:
   retrieving, from a storage element by a waveform analysis application, a plurality of samples representing a plethysmographic waveform of a patient;
   calculating, by the waveform analysis application, a power spectrum density for the plurality of samples representing the plethysmographic waveform of the patient;
   detecting, by the waveform analysis application, a first wave peak of the power spectrum density and a second wave peak of the power spectrum density, wherein the first wave peak is indicative of a respiratory activity of the patient and the second wave peak is indicative of a heart rate of the patient;
   determining, by the waveform analysis application, a proportion of the first wave peak to the second wave peak, and
   triggering, by the waveform analysis application and responsive to the determined proportion being within a predetermined range, an alarm to alert the patient or a health care provider to the presence of pulsus paradoxus.

2. The method of claim 1, wherein determining the proportion comprises comparing a height of the first wave peak to a height of the second wave peak and the predetermined range is from 0.6 to 3.

3. The method of claim 1, wherein determining the proportion of the first wave to the second wave comprises comparing an area under the first wave peak to an area under the second wave peak.

4. The method of claim 1, further comprising:
   retrieving, from the storage element by the waveform analysis application, a second plurality of samples representing an electrocardiogram (ECG) waveform of a patient; and
   comparing the plurality of samples representing the plethysmographic waveform and the second plurality of samples representing the ECG waveform to confirm the presence of pulsus paradoxus.

5. The method of claim 1, further comprising comparing the power spectrum density for the plurality of samples representing the plethysmographic waveform to a power spectrum density for a plurality of samples representing a respiratory waveform to confirm the presence of pulsus paradoxus.

6. A system comprising:
   at least one patient monitoring device to record data representing a physiological condition of a patient over a period of time, wherein the data comprises a plurality of samples corresponding to a respiratory activity and a plurality of samples corresponding to a heart rate;
   a database to store the data generated by the at least one patient monitoring device; and
   a waveform analysis application to:
      retrieve, from the database, the plurality of samples corresponding to the respiratory activity and the plurality of sample corresponding to the heart rate;
      calculate, using fast-Fourier transform analysis, a first wave peak of the plurality of samples corresponding to the respiratory activity and a second wave peak of the plurality of samples corresponding to the heart rate;
      compare a height of the first wave peak and to a height of the second wave peak;
      detect an abnormality indicative of pulsus paradoxus based on the comparison; and
      triggering, responsive to detecting the abnormality, an alarm to alert a health care provider of the abnormality.

7. The system of claim 6, wherein the abnormality indicative of pulsus paradoxus is identified when a proportion of the height of the first wave peak to the height of the second wave peak is from 0.6 to 3.

8. The system of claim 6, wherein an abnormality indicative of pulsus paradoxus is detected when the height of the first wave peak from a baseline is different than the height of the second wave peak from the baseline.

9. The system of claim 6, further comprising:
   an interface for displaying the first wave peak and the second wave peak.

10. The system of claim 6, wherein the at least one patient monitoring device is a pulse oximeter.

11. The system of claim 6, further comprising a first patient monitor configured to record plurality of samples corresponding to the respiratory activity and a second patient monitor configured to record the plurality of samples corresponding to the heart rate.

12. The system of claim 6, wherein the first wave peak and the second wave peak are in the form of a power spectrum density.

13. The system of claim 6, wherein the at least one patient monitor is an electrocardiogram.

14. The system of claim 6, wherein the plurality of samples corresponding to the heart rate form a plethysmographic waveform and the plethysmographic waveform is compared to data corresponding to a sinus rhythm to confirm the presence of the abnormality indicative of pulsus paradoxus.

* * * * *